(12) United States Patent
Lee et al.

(10) Patent No.: US 9,700,595 B2
(45) Date of Patent: Jul. 11, 2017

(54) LIQUID FORMULATION OF A FUSION PROTEIN COMPRISING TNFR AND FC REGION

(71) Applicant: ARES TRADING SA, Aubonne (CH)

(72) Inventors: Jung Tae Lee, Yuseong-gu (KR); In Hyuk Kim, Daejeon (KR); Jae Keun Yu, Incheon (KR); Jung Yim Yim, Daejeon (KR); Myeong Hyeon Jeong, Daejeon (KR); Yong Ho Ahn, Daejeon (KR)

(73) Assignee: ARES TRADING SA, Aubonne (CH)

( * ) Notice: Subject to any disclaimer, the term of this patent is extended or adjusted under 35 U.S.C. 154(b) by 0 days.

(21) Appl. No.: 15/038,953

(22) PCT Filed: Nov. 28, 2014

(86) PCT No.: PCT/KR2014/011540
§ 371 (c)(1),
(2) Date: May 24, 2016

(87) PCT Pub. No.: WO2015/080513
PCT Pub. Date: Jun. 4, 2015

(65) Prior Publication Data
US 2017/0028020 A1    Feb. 2, 2017

(30) Foreign Application Priority Data

Nov. 29, 2013 (KR) .......................... 10-2013-0148028

(51) Int. Cl.
| | |
|---|---|
| A61K 38/17 | (2006.01) |
| A61K 9/08 | (2006.01) |
| A61K 47/02 | (2006.01) |
| A61K 47/18 | (2017.01) |
| A61K 47/26 | (2006.01) |
| A61K 47/22 | (2006.01) |
| C07K 14/705 | (2006.01) |

(52) U.S. Cl.
CPC ............ *A61K 38/1793* (2013.01); *A61K 9/08* (2013.01); *A61K 47/02* (2013.01); *A61K 47/183* (2013.01); *A61K 47/22* (2013.01); *A61K 47/26* (2013.01); *C07K 14/70578* (2013.01); *C07K 2319/30* (2013.01)

(58) Field of Classification Search
CPC .... A61K 38/1793; A61K 47/02; A61K 47/22; A61K 47/183; A61K 47/26; A61K 9/08; C07K 14/70578; C07K 2319/30
See application file for complete search history.

(56) References Cited

U.S. PATENT DOCUMENTS

| 7,276,477 B2 | 10/2007 | Osslund et al. |
| 2013/0022625 A1 | 1/2013 | Igawa et al. |

FOREIGN PATENT DOCUMENTS

| WO | 2012143418 A1 | 10/2012 |
| WO | 2012165917 A1 | 12/2012 |
| WO | 2013059405 A1 | 4/2013 |
| WO | 2015080513 A1 | 6/2015 |

OTHER PUBLICATIONS

PCT/KR2014/011540, International Search Report, mailed Feb. 27, 2015, 6 pages.

*Primary Examiner* — Robert Landsman
(74) *Attorney, Agent, or Firm* — Carter, DeLuca, Farrell & Schmidt, LLP

(57) ABSTRACT

The present invention relates to a liquid formulation comprising a TNFR-Fc fusion protein and a stabilizer, in which the fusion protein comprises TNFR (tumor necrosis factor receptor) or a fragment thereof and an immunoglobulin Fc region, and the stabilizer comprises one or more amino acids selected from the group consisting of proline and histidine, a buffer solution, and an isotonic agent containing sodium chloride (NaCl) and sucrose, and a preparation method of the liquid formulation. The liquid formulation according to the present invention provides excellent storage stability because long-term storage of TNFR-Fc fusion protein (etanercept) is possible and particular storage conditions are not needed. Since the liquid formulation of the present invention shows excellent storage stability even though the formulation is simple, it is more economical than other stabilizers or lyophilized formulations, and thus the formulation can be effectively applied for uses wherein treatment of TNFR-Fc fusion protein (etanercept) is beneficial.

24 Claims, 2 Drawing Sheets

[Fig. 1]

```
LPAQVAFTPY APEPGSTCRL REYYDQTAQM CCSKCSPGQH AKVFCTKTSD TVCDSCEDST    60
YTQLWNWVPE CLSCGSRCSS DQVETQACTR EQNRICTCRP GWYCALSKQE GCRLCAPLRK   120
CRPGFGVARP GTETSDVVCK PCAPGTFSDT TSSTDICRPH QICNVVAIPG DASMDAVCTS   180
TSPTRSMAPG AVHLPQPVST RSQHTQPTPE PSTAPSTSFL LPMGPSPPAE GSTGDEPKSC   240
DKTHTCPPCP APELLGGPSV FLFPPKPKDT LMISRTPEVT CVVVDVSHED PEVKFNWYVD   300
GVEVHNAKTK PREEQYDSTY RVVSVLTVLH QDWLNGKEYK CKVSNKALPA PIEKTISKAK   360
GQPREPQVYT LPPSREEMTK NQVSLTCLVK GFYPSDIAVE WESNGQPENN YKTTPPVLDS   420
DGSFFLYSKL TVDKSRWQQG NVFSCSVMHE ALHNHYTQKS LSLSPG
```

[Fig. 2a]

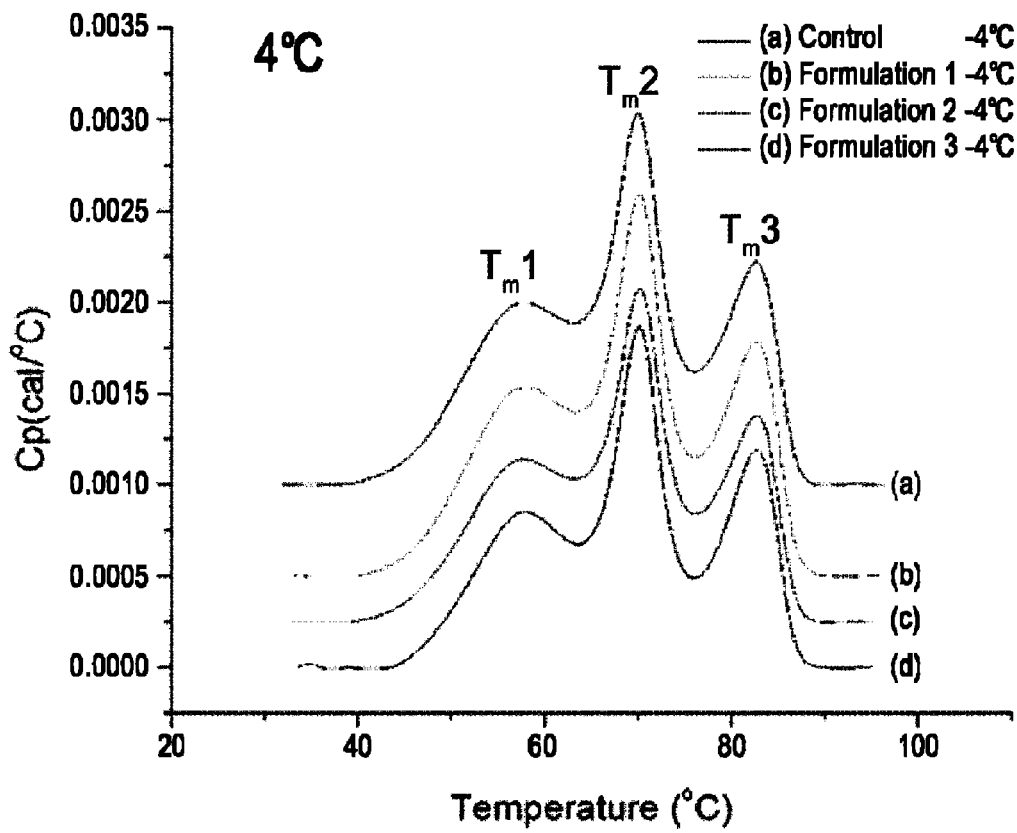

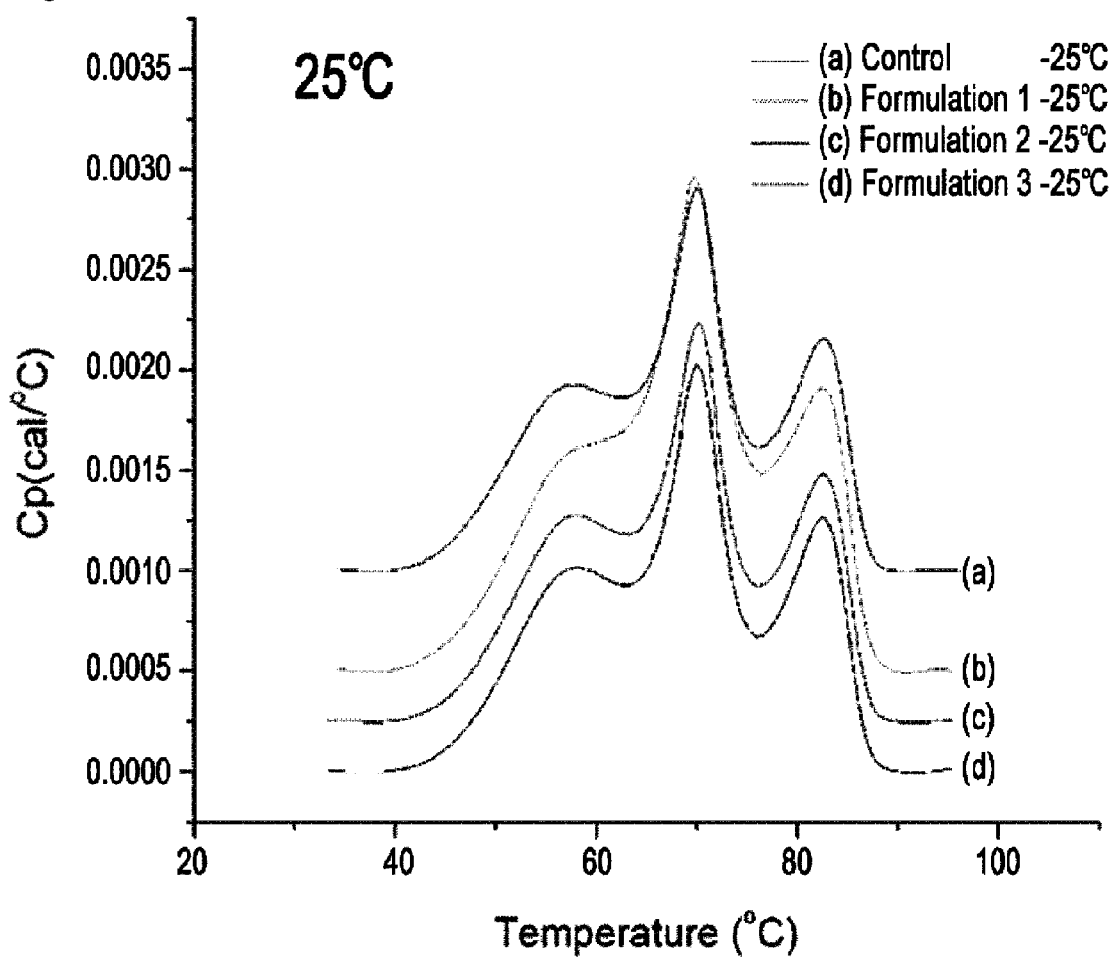

LIQUID FORMULATION OF A FUSION PROTEIN COMPRISING TNFR AND FC REGION

CROSS-REFERENCE TO RELATED APPLICATIONS

This application is a national stage filing of International Application No. PCT/KR2014/011540, filed Nov. 28, 2014, which claims benefit of priority pursuant to Korean Application KR 10-2013-0148028, filed Nov. 29, 2013. The entire disclosures of the afore-mentioned patent applications are incorporated herein by reference.

SEQUENCE LISTING

The instant application contains a Sequence Listing, which has been filed electronically in ASCII format and is hereby incorporated by reference in its entirety. Said ASCII copy, created on Sep. 9, 2016, is named 2300-403_SL.txt and is 4,528 bytes in size.

TECHNICAL FIELD

The present invention relates to a liquid formulation comprising a TNFR-Fc fusion protein and a stabilizer, in which the fusion protein comprises TNFR (tumor necrosis factor receptor) or a fragment thereof and an immunoglobulin Fc region, and the stabilizer comprises one or more amino acids selected from the group consisting of proline and histidine, a buffer solution, and an isotonic agent containing sodium chloride (NaCl) and sucrose, and a preparation method of the liquid formulation.

BACKGROUND ART

In general, chemical and physical denaturation of protein drugs can be easily caused by unfavorable temperature, shear stress, vibration, freeze-thawing, UV exposure, excessive pH change, organic solvents, microbial contamination, etc. Chemical denaturation includes dimer dissociation, oxidation, deamidation, isomerization, and polymerization, which are influenced by the amino acids constituting the protein and conditions of the solvent containing the protein (salt, pH and temperature). Physical denaturation includes loss of tertiary structure, covalent/non-covalent aggregation and adhesion of monomers, which are influenced by hydrophobic patches on the protein surface changed by protein-containing surrounding environments such as solvents, complex protein structures such as charge distribution, and thermal stability.

The physical or chemical denaturation of a protein including an antibody causes loss of its physiological activities. Since the denaturation is an irreversible process, proteins, once denatured, may not recover their native properties, leading to a reduction in their therapeutic efficacies. It has been also suggested that phenomenon such as aggregation of monomers causes immune responses. Therefore, many studies have been conducted on formulations containing a physiologically effective amount of protein without aggregates (Ishikawa et al., Biol. Pharm. Bull., 33(8): 1413-1417, 2010).

There are many methods available for preventing protein denaturation in liquid formulations. In some protein drugs, the stability problems are addressed via lyophilization. However, the lyophilization process causes stress related to freezing and drying, such as formation of ice crystals, pH change, and high concentration of solute, and these stresses may cause protein denaturation. In addition, since a large-capacity lyophilizer is needed for the lyophilization process during production, high production costs arise during large scale production. Dissolving the lyophilized product in sterile aqueous media before use also poses an inconvenience.

As an alternative to solve these limitations, a stabilizer is added to liquid formulations for the improvement of protein stability. Surfactants, serum albumins, polysaccharides, amino acids, polymers, salts or the like are known as stabilizers used in protein drugs (Wang, Int. J. Pharm., 185: 129-188, 1999; Wang et al., J. Pharm. Sci., 96(1): 1-26, 2007).

In order to prepare stable formulations of the drugs, however, appropriate stabilizers should be used considering the physicochemical properties of each active ingredient. When the stabilizers are used in combination, competition therebetween and adverse effects may lead to undesirable effects. In addition, the concentrations of proteins should be within the range suitable for the stabilization, and in particular, to prepare high concentrations of protein drugs, much effort and caution is required to stabilize proteins in solutions (Shire et al., J. Pharm. Sci., 93(6): 1390-1402, 2004).

Meanwhile, etanercept is a biological modulator that functions as a competitive inhibitor of TNF-α, binding to cell surface TNF-α receptor, to inhibit TNF-α mediated immune responses. Etanercept is a macromolecule with a molecular weight of 150 kDa, and is a homodimer of two fusion proteins linked by disulfide bond, each fusion protein consisting of a human soluble p75 TNF (tumor necrosis factor) receptor coupled to the Fc portion of human immunoglobulin G subclass 1 (Goldenberg, Clinical Therapeutics, 21(1): 75-87, 1999; Moreland et al., Ann. Intern. Med., 130(6): 478-486, 1999).

This is marketed by Amgen under the trade name of Enbrel in 2002. Etanercept is a TNF-α inhibitor used to treat rheumatoid arthritis, psoriasis, and ankylosing spondylitis, and is under clinical trials for the treatment of vasculitis, Alzheimer's disease, and Crohn's disease.

Formulation stabilization technologies for TNFR-Fc fusion proteins such as etanercept aim to develop a liquid formulation for minimizing protein denaturation which may occur during production, storage, and transportation, and maintaining their activity for a long period of time to be identical to that of conventional protein drugs, but it has been difficult to develop satisfactory liquid formulations. Therefore, there is an urgent need to develop a new liquid formulation which is able to stably maintain the activity of TNFR-Fc fusion protein (etanercept) for a long period of time and which is more effective in stabilization of TNFR-Fc fusion protein (etanercept) than the known formulations, including arginine as disclosed in U.S. Pat. No. 7,648,702.

DISCLOSURE

Technical Problem

Accordingly, the present inventors have made many efforts to develop a method for preparing a liquid formulation capable of stably maintaining the activity of etanercept. The present invention provides that a stabilizer comprising one or more amino acids selected from the group consisting of proline and histidine shows remarkable effects on the stabilization of etanercept in a solution, even when used at a lower concentration than the concentrations used for known stabilizers comprising single amino acid or mixed amino acids, thereby completing the present invention.

Technical Solution

An object of the present invention is to provide a stable liquid formulation comprising a TNFR-Fc fusion protein and a stabilizer, in which the TNFR-Fc fusion protein is a fusion protein comprising TNFR (tumor necrosis factor receptor) or a fragment thereof and an immunoglobulin Fc region, and the stabilizer comprises one or more amino acids selected from the group consisting of proline and histidine, a buffer solution, and an isotonic agent, preferably containing sodium chloride (NaCl) and sucrose.

Another object of the present invention is to provide a preparation method of the liquid formulation.

Advantageous Effects

A liquid formulation according to the present invention provides excellent storage stability because long-term storage of TNFR-Fc fusion protein (etanercept) is possible and particular storage conditions are not needed. Since the liquid formulation of the present invention shows excellent storage stability even though the formulation is simple, it is more economical than other stabilized or lyophilized formulations, and thus the formulation can be effectively used in treatments with TNFR-Fc fusion protein (etanercept).

DESCRIPTION OF DRAWINGS

FIG. 1, shows the amino acid sequence (SEQ ID No. 1) for the p75 sTNFR-Fc fusion protein (etanercept).

FIGS. 2a and 2b, show the Differential Scanning calorimetry (DSC) graphs for the formulations 1, 2, 3, and control as described in Example 3. FIG. 2a shows the DSC graphs at 4° C. FIG. 2b shows the DSC graphs at 25° C. The DSC thermograms of FIGS. 2a and 2b show the results for etanercept formulations containing either Arginine and Histidine (formulation 1) or Proline and Histidine (formulations 2 and 3) at the 6 month time point.

BEST MODE

In one aspect to achieve the above objects, the present invention provides a liquid formulation comprising a TNFR-Fc fusion protein and a stabilizer, in which the fusion protein comprises TNFR (tumor necrosis factor receptor) or a fragment thereof and an immunoglobulin Fc region, and the stabilizer comprises one or more amino acids selected from the group consisting of proline and histidine, a buffer solution, and an isotonic agent, preferably containing sodium chloride (NaCl) and sucrose.

The fusion protein comprising TNFR or a fragment thereof and immunoglobulin Fc region may be etanercept (recombinant p75 sTNFR-Fc fusion protein), in particular, represented by an amino acid sequence of SEQ ID NO. 1. Further, the fusion protein may be a mutated fusion protein which is prepared by amino acid substitution, deletion or insertion in the amino acid sequence of SEQ ID NO. 1, or a peptide analogue showing an activity similar to that of etanercept. The liquid formulation of the present invention is a stabilized liquid formulation or a stable liquid formulation, which comprises one or more amino acids selected from the group consisting of proline and histidine or a pharmaceutically acceptable salt thereof, thereby reducing by-product formation of TNFR-Fc fusion protein (etanercept) and stably maintaining its activity for a long period of time.

As used herein, the term "fusion protein comprising TNFR and immunoglobulin Fc region" refers to a recombinant protein prepared by fusion of tumor necrosis factor receptor (TNFR) or a fragment thereof and an immunoglobulin Fc region, and in particular, the immunoglobulin Fc region may be derived from an immunoglobulin Fc region of IgG1. Preferably, the fusion protein may be etanercept, and represented by the amino acid sequence of SEQ ID NO. 1.

As used herein, the term "etanercept (recombinant p75 sTNFR:Fc fusion protein)" refers to a protein which is a homodimer form of two fusion proteins linked by disulfide bonds, each fusion protein consisting of a human soluble 75 kilodalton (p75) TNF receptor coupled to the Fc portion of human immunoglobulin G (IgG1) subclass 1.

More specifically, etanercept is a homodimer form of two fusion proteins linked by 3 disulfide bonds, each fusion protein consisting of the extracellular ligand-binding portion of the human soluble p75 TNF receptor linked to the Fc portion of human IgG1. The Fc component of etanercept contains a CH2 domain, a CH3 domain and a hinge region, but not a CH1 domain of IgG1. The etanercept may have a molecular weight of approximately 150 kDa. This etanercept may be currently sold under the trade name ENBREL® (Amgen Inc., Thousand Oaks, Calif.), and have CAS number 185243-69-0.

The fusion protein comprising TNFR or a fragment thereof and immunoglobulin Fc region of the present invention, in particular, etanercept may be produced by recombinant DNA technology in a cell expression system, but is not limited thereto.

The etanercept of the present invention is a biological modulator that functions as a competitive inhibitor of TNF-α, binding to cell surface TNF-α receptor, to inhibit TNF-α mediated immune responses, and is used to treat rheumatoid arthritis, psoriasis, and ankylosing spondylitis, and is under clinical trials for the treatment of vasculitis, Alzheimer's disease, and Crohn's disease.

In the liquid formulation of the present invention, the fusion protein comprising TNFR or a fragment thereof and immunoglobulin Fc region of the present invention, in particular, etanercept may be included in a pharmaceutically effective amount, and in an amount of 1 to 100 mg/mL, preferably 20 to 55 mg/mL, and more preferably 30 to 55 mg/mL.

As used herein, the term "stabilized liquid formulation" or "stable liquid formulation" refers to a formulation that retains the physical and chemical identity and integrity of the therapeutically active ingredient, that is, the fusion protein of the present invention, in particular, etanercept, during storage in a solution. An analytical measurement of the stability of the fusion protein of the present invention, in particular, etanercept may be performed by protein stability assay widely known in the art. The stability may be measured at a predetermined temperature for a predetermined time. For rapid assay, the formulation may be stored at a higher or "elevated" temperature, for example, 40° C. for 2 weeks to 1 month or longer, and its time-dependent stability is measured at this time.

As used herein, the term "stabilizer" refers to a specific chemical compound or a composition that interacts with a biological molecule and/or a general pharmaceutical excipient in a formulation to improve its stability. The stabilizer generally protects proteins from air/solution interface-induced stress and solution/surface-induced stress which cause protein aggregation. In the present invention, the stabilizer is a component that reduces by-product formation of the fusion protein of the present invention, in particular, etanercept, during storage in a solution to maintain its activity for a long period of time. Preferably, the stabilizer comprises one or more amino acids selected from the group consisting of proline and histidine.

The amino acid of the present invention may include both L-amino acids and D-amino acids.

As the stabilizer of the present invention, not only the amino acids themselves such as proline and histidine, but also analogues, solvates, hydrates, stereoisomers, and pharmaceutically acceptable salts thereof are within the scope of the present invention as long as they show the substantially identical effect.

As used herein, the term "by-product" refers to an undesirable product that lowers or reduces the ratio of the therapeutically active ingredient, TNFR-Fc fusion protein (etanercept), in the formulation. The typical by-product include "low molecular weight products" resulting from denaturation of the TNFR-Fc fusion protein (etanercept) by deamination or hydrolysis, "high molecular weight products" such as oligomers and aggregates, or mixtures thereof.

As used herein, the term "high molecular weight products" includes TNFR-Fc fusion protein (etanercept) fragments that are subsequently aggregated by denaturation (e.g., produced by polypeptide degradation due to deamination or hydrolysis) or mixtures thereof. Typically, the high molecular weight products are complexes having higher molecular weights than the therapeutic monomer TNFR-Fc fusion protein (etanercept), and may have a molecular weight of more than approximately 150 kDa.

As used herein, the term "low molecular weight products" includes, for example, therapeutic polypeptides produced by deamination or hydrolysis, namely, TNFR-Fc fusion protein (etanercept) fragments. Typically, the low molecular weight products are complexes having lower molecular weights than the therapeutic monomer TNFR-Fc fusion protein (etanercept), and may have a molecular weight of less than approximately 150 kDa.

The liquid formulation of the present invention comprises one or more amino acids, selected from the group consisting of proline and histidine, as stabilizers. Other additional amino acids such as for example glutamic acid, may be added to stabilize the formulation. Preferably, the liquid formulation comprises proline or histidine alone, or both amino acids of proline and histidine. In the combination, the pharmaceutically acceptable salts of proline or histidine may be further included, or modified forms of proline and histidine or their pharmaceutically acceptable salts may be included. Preferably, the liquid formulation comprises a mixture of amino acids of proline and histidine.

In the present invention, the proline concentration may be in the range from 1 to 10 mM, preferably from 1 to 9 mM, more preferably from 3 to 9 mM, even more preferably from 3 to 6 mM, and the histidine concentration may be in the range from 0.01 to 5 mM, preferably from 0.01 to 0.1 mM, more preferably from 0.03 to 0.1 mM, even more preferably from 0.03 to 0.09 mM, even more preferably from 0.06 to 0.09 mM, or even more preferably about 0.09 mM in the stabilizer. Specifically, in a mixture of the amino acids of proline and histidine included as a stabilizer, the proline concentration may be in the range from 1 to 10 mM, preferably from 1 to 9 mM, more preferably from 3 to 9 mM, even more preferably from 3 to 6 mM, and the histidine concentration may be in the range from 0.01 to 5 mM, preferably from 0.01 to 0.1 mM, more preferably from 0.03 to 0.1 mM, even more preferably from 0.03 to 0.09 mM, even more preferably from 0.06 to 0.09 mM, or even more preferably about 0.09 mM. The addition of additional amino acids, such as glutamic acid, may be in the range from 1 to 20 mM, preferably from 5 to 15 mM, more preferably from 10 to 15 mM. When combined with the mixture of proline and histidine, the concentration of glutamic acid may be in the range from 1 to 20 mM, preferably from 5 to 15 mM, more preferably from 10 to 15 mM.

In one specific embodiment of the present invention, in the preparation of the stabilized liquid formulation for TNFR-Fc fusion protein (etanercept), liquid formulations were prepared by varying the amino acid combination and conditions of the isotonic agent in order to develop a liquid formulation which has advantages over known liquid formulations, including arginine, as the stabilized liquid formulation of etanercept (U.S. Pat. No. 7,648,702), and their stabilizing effects were examined.

As a result, the formulations comprising one or more amino acids selected from the group consisting of proline and histidine were found to show remarkable effects of stabilizing etanercept in a solution by preventing its denaturation during storage at a high temperature (Formulation 4 and Formulation 5, Formulation 7 and Formulation 8 of Table 1, Formulation 2 and Formulation 3 of Table 4, Formulation 2 to Formulation 4 and Formulation 6 to Formulation 7 of Table 7). In particular, the formulations comprising a mixture of the amino acids of proline and histidine (Formulation 5 and Formulation 8 of Table 1, Formulation 2 and Formulation 3 of Table 4, Formulation 2 to Formulation 4 and Formulation 6 to Formulation 7 of Table 7) showed more excellent stabilizing effect than the control formulation.

That is, the present invention first demonstrated that a stabilizer comprising one or more amino acids selected from the group consisting of proline and histidine shows remarkable effects on the stabilization of etanercept in a solution, even when used at a lower concentration (6.1 mM) than the concentration (10 mM or more) of the known stabilizers using single amino acid or mixture of amino acids.

The liquid formulation according to the present invention may further comprise any material which is generally contained in liquid formulations of protein drugs or antibody drugs, as long as it does not deteriorates the function of improving stability of TNFR-Fc fusion protein (etanercept) by adding a stabilizer comprising one or more amino acids selected from the group consisting of proline and histidine.

As used herein, the term "buffer solution" refers to the component that improves isotonicity and chemical stability of the formulation, and functions to maintain physiologically suitable pH. The buffer prevents a rapid pH change of the liquid formulation to maintain pH of the solution for the stabilization of TNFR-Fc fusion protein (etanercept). Preferred examples of the buffer solution include an aqueous solution of citrate, phosphate, succinate, tartrate, fumarate, gluconate, oxalate, lactate, acetate, histidine, or Tris, etc., but are not limited thereto. In the specific embodiment, the buffer is an aqueous citrate-phosphate buffer solution. The buffer may be used either alone or in combinations of two or more thereof.

The liquid formulation of the present invent ion may have pH of approximately 5 to 7.5 or pH of approximately 5.8 to 6.8. In particular, the formulation has pH of approximately 6.0 to 6.6. If necessary, pH may be adjusted by techniques known in the art. The buffer solution may exist at a concentration of 0.1 to 100 mM, preferably 1 to 50 mM, and more preferably, 10 to 35 mM. Preferably, water for injection is used in the aqueous buffer solution of the present invention.

As used herein, the term "isotonic agent" refers to a component that functions to partially maintain isotonicity of the formulation and the protein level, and partially maintain the level, ratio, or proportion of the therapeutically active polypeptide present in the formulation. The isotonic agent maintains the same osmotic pressure as blood plasma, and so can be intravenously injected into a subject without changing the osmotic pressure of the subject's blood plasma. In one embodiment according to the present invent ion, the osmotic pressure is suitable for intravenous injection of the formulation of the present invention. Often, the isotonic agent serves as a bulking agent as well. As such, the isotonic agent may allow the protein to overcome various stresses such as freezing and shear.

The isotonic agent serves to maintain the proper osmotic pressure in the body, when TNFR-Fc fusion protein (etanercept) in the solution is administered into the body. Examples of the isotonic agent may include the commonly used sodium chloride, potassium chloride, boric acid, sodium borate, mannitol, glycerin, propylene glycol, polyethylene glycol, maltose, sucrose, erythritol, arabitol, xylitol, sorbitol, glucose, etc., but are not limited thereto. These isotonic agents may be used either alone or in combinations of two or more thereof. In the present invention, the isotonic agents may be those comprising sodium chloride and sucrose. The isotonic agent of the present invention allows the solution to maintain an osmotic pressure of 250 to 350 mOsm, and it may comprise preferably 1 to 1000 mM sodium chloride and/or 0.01 to 3% sucrose, more preferably 50 to 250 mM sodium chloride and/or 0.01 to 1.5% sucrose, and even more preferably 105 to 150 mM sodium chloride and/or 0.01 to 1.5% sucrose. When sodium chloride and sucrose are used in the formulation of the present invention, the sodium chloride concentration can be from 1 to 1000 mM, preferably from 50 to 250 mM, more preferably from 100 to 150 mM, even more preferably from 105 to 150 mM, yet even more preferably from 115 to 140 mM, even more preferably from 115 to 130 mM, and the amount of sucrose in the formulation can be from 0.01 to 3% by weight of the total formulation, preferably from 0.01 to 1.5 weight %, more preferably from 0.1 to 1.0 weight %, even more preferably the amount of sucrose in the formulation is selected from 0.1 weight %, 0.5 weight %, and 1.0 weight %.

In one specific embodiment of the present invention, as the isotonic agent in the liquid formulation of the present invention, sodium chloride and sucrose were used, and formulations comprising 115 mM sodium chloride and 1.0% sucrose (Formulation 1 to Formulation 5 of Table 1) or formulations comprising 115 mM sodium chloride and 0.5% sucrose (Formulation 1 to Formulation 4 of Table 7) and formulations comprising 140 mM sodium chloride and 0.1% sucrose (Formulation 6 to Formulation 8 of Table 1) or formulations comprising 130 mM sodium chloride and 0.1% sucrose (Formulation 5 to Formulation 7 of Table 7) were prepared and their stabilizing effects were compared with that of the control formulation (100 mM of sodium chloride, 1.0% sucrose).

As a result, compared to the known etanercept formulation, the formulations of the present invention using the isotonic agents which were prepared by varying concentrations of sucrose and sodium chloride were found to show improvement in the etanercept stability due to the increased sodium chloride concentration and the reduced sucrose concentration in the isotonic agent.

The liquid formulation according to the present invention may further comprise a pharmaceutically acceptable excipient, and examples of the excipient may include sugars and polyols, surfactants, polymers or the like. Examples of the sugars and polyols may include sucrose, trehalose, lactose, maltose, galactose, mannitol, sorbitol, glycerol, etc., examples of the surfactants may include non-ionic surfactants such as polysorbate 20, polysorbate 80, poloxamer, etc., and examples of the polymers may include dextran, polyethylene glycol, carboxyl methylcellulose, hyaluronic acid, cyclodextrin, etc.

The liquid formulation according to the present invention may further comprise a preservative. The preservative refers to a chemical that is added to pharmaceutical formulations as an antimicrobial agent. Examples of the preservative may include benzalkonium chloride, benzethonium, chlorhexidine, phenol, m-cresol, benzyl alcohol, methylparaben, propylparaben, chlorobutanol, o-cresol, p-cresol, chloro-cresol, phenylmercuric nitrate, thimerosal, benzoic acid, etc., but are not limited thereto. These preservatives may be used either alone or in combinations of two or more thereof.

The liquid formulation of the present invention may be a stable liquid formulation comprising TNFR-Fc fusion protein in a pharmaceutically effective amount and the stabilizer, in which the TNFR-Fc fusion protein ("etanercept") is represented by the amino acid sequence of SEQ ID NO. 1, and the stabilizer comprises a citrate-phosphate buffer solution, sodium chloride, sucrose, and a mixture of amino acids of proline and histidine. In particular, the liquid formulation of the present invention may be a liquid formulation comprising 30 to 55 mg/mL of TNFR-Fc fusion protein, and 10 to 35 mM citrate-phosphate buffer solution, 105 to 125 mM NaCl, 0.5 to 1.5% sucrose, 1 to 9 mM proline and 0.01 to 0.1 mM histidine at pH 6.3; or a liquid formulation comprising 30 to 55 mg/mL of TNFR-Fc fusion protein, and 10 to 35 mM citrate-phosphate buffer solution, 120 to 150 mM NaCl, 0.01 to 0.5% sucrose, 1 to 9 mM proline and 0.01 to 0.1 mM histidine at pH 6.3.

In specific embodiments of the present invention, the following liquid formulations are provided.

Liquid formulation comprising 50 mg/mL of TNFR-Fc fusion protein, 25 mM citrate-phosphate buffer solution, 115 mM NaCl, 0.5% sucrose, 6 mM proline and 0.09 mM histidine at pH 6.3 (Formulation 3 of Table 7).

Liquid formulation comprising 50 mg/mL of TNFR-Fc fusion protein, 25 mM citrate-phosphate buffer solution, 130 mM NaCl, 0.1% sucrose, 6 mM proline and 0.09 mM histidine at pH 6.3 (Formulation 7 of Table 7).

Liquid formulation comprising 50 mg/mL of TNFR-Fc fusion protein, 25 mM citrate-phosphate buffer solution, 100 mM NaCl, 1.0% sucrose, 10 mM proline, 5 mM histidine, and 10 mM Glutamic acid at pH 6.3 (Formulation 10 of Table 1).

The formulation of the present invention can be used for treatment of a disease in which etanercept is therapeutically effective. Etanercept is a biological modulator to inhibit TNF-α mediated immune responses, and the formulation of the present invention can be used to treat rheumatoid arthritis, psoriasis, ankylosing spondylitis, vasculitis, Alzheimer's disease, or Crohn's disease, but is not limited thereto.

The formulation according to the present invention may be administered into the body via oral or parenteral route, i.e., subcutaneous, intramuscular, intraperitoneal, intrasternal, transdermal, and intravenous injection, but is not limited thereto.

In another aspect, the present invention provides a preparation method of the liquid formulation.

The liquid formulation of the present invention may be prepared by a method comprising the steps of preparing etanercept; and mixing etanercept prepared in the above step with a stabilizer comprising one or more amino acids selected from the group consisting of proline and histidine, a buffer solution, and an isotonic agent, preferably containing sodium chloride (NaCl) and sucrose. In the above described preparation method the mixing step can comprise exchanging the solution in which etanercept is prepared with a solution comprising the stabilizer.

In still another aspect, the present invention provides a pharmaceutical composition comprising the liquid formulation for prevention or treatment of disorders in which TNFα activity is detrimental.

The liquid formulation is the same as described above.

As used herein, the term "disorders in which TNFα activity is detrimental" include diseases and other disorders in which the presence of TNFα in a subject suffering from the disorder has been shown to be or is suspected of being either responsible for the pathophysiology of the disorder or a factor that contributes to a worsening of the disorder. In the present invention, examples of the disorders in which TNFα activity is detrimental may include inflammatory diseases such as sepsis, autoimmune diseases, in particular, rheumatoid arthritis, rheumatoid spondylitis, osteoarthritis, gouty arthritis, allergy, multiple sclerosis, autoimmune diabetes, autoimmune uveitis, and nephrotic syndrome, infectious diseases, allograft rejection and graft-versus-host disease (GVHD), malignant tumors, pulmonary disorders, intestinal disorders, cardiac disorders, etc., but are not limited thereto.

The disorders in which TNFα activity is detrimental can be prevented or treated by administering the composition of the present invention into a subject.

As used herein, the term "treatment" refers to any action resulting in improvements in symptoms of the disorders in which TNFα activity is detrimental or the beneficial alteration of the disorders in which TNFα activity is detrimental owing to the administration of the composition of the present invention, and the term "prevention" refers to any action resulting in the suppression or delay of the onset of the disorders in which TNFα activity is detrimental owing to the administration of the composition. The prevention or treatment can be applied to any mammal having the disorders in which TNFα activity is detrimental, for example, humans and primates as well as livestock such as cow, pig, sheep, horse, dog, cat, etc. without limitation, and preferably humans.

As used herein, the term "administration" refers to the introduction of a predetermined amount of substance into a patient by a certain suitable method. The administration route of the composition may be any of the common routes, as long as it is able to reach a desired tissue. The administration route may be intraperitoneal, intravenous, intramuscular, subcutaneous, intracutaneous, oral, topical, intranasal, intrapulmonary, or rectal route, but is not limited thereto. However, since peptides are digested upon oral administration, the active ingredient of a composition for oral administration should be preferably coated or formulated for protection against degradation in the stomach. Preferably, it may be administered in an injectable formulation. In addition, the composition may be administered with the aid of any device that helps transmit of the active ingredient into target cells.

Further, the pharmaceutical composition of the present invention is determined depending on the kind of the active ingredient, together with various related factors such as the disease to be treated, the route of administration, the patient's age, sex, and body weight, and severity of the disease.

Further, the pharmaceutical composition of the present invention may comprise a pharmaceutically acceptable carrier. As used herein, the term "pharmaceutically acceptable carrier" refers to a carrier or diluent that does not cause significant irritation to an organism and does not abrogate the biological activity and properties of the administered compound. For oral administration, a binder, a lubricant, a disintegrator, an excipient, a solubilizer, a dispersing agent, a stabilizer, a suspending agent, a coloring agent, a perfume or the like may be used. For injectable administration, a buffering agent, a preserving agent, an analgesic, a solubilizer, an isotonic agent, a stabilizer or the like may be used in combination. For topical administration, a base, an excipient, a lubricant, a preserving agent or the like may be used. The pharmaceutical composition of the present invention may be prepared into various formulations by mixing it with the above described pharmaceutically acceptable carriers. For example, for oral administration, the pharmaceutical composition may be prepared in the form of a tablet, a troche, a capsule, an elixir, a suspension, a syrup, a wafer or the like. The injectable composition may be formulated in unit dosage ample or multi dosage form. It can be also prepared as a solution, a suspension, a tablet, a pill, a capsule, a sustained release formulation or the like.

The liquid formulation of the present invention comprises a therapeutically effective amount of TNFR-Fc fusion protein (etanercept). For example, a therapeutically effective amount of etanercept (Enbrel) is generally 25 to 100 mg per week.

In still another aspect, the present invention provides a method for preventing or treating disorders in which TNFα activity is detrimental, comprising the step of administering a composition comprising the liquid formulation into a subject having the disorder in which TNFα activity is detrimental.

Since the composition comprising the liquid formulation of the present invention is able to stably maintain high concentration of TNFR-Fc fusion protein (etanercept) for a long period of time, long-term storage is possible and particular storage conditions are not needed. Therefore, it can be widely used for preventing or treating disorders in which TNFα activity is detrimental.

One embodiment of the invention is a liquid formulation comprising a TNFR-Fc fusion protein, one or more amino acids, a buffer solution, and an isotonic agent, wherein the fusion protein comprises TNFR (tumor necrosis factor receptor) or a fragment thereof and an immunoglobulin Fc region, and the one or more amino acids are selected from the group consisting of proline and histidine and glutamic acid.

A second embodiment is the liquid formulation according to first embodiment, wherein the fusion protein is etanercept.

A third embodiment is the liquid formulation according to first embodiment, wherein the fusion protein is has the amino acid sequence of SEQ ID NO. 1.

A fourth embodiment is the liquid formulation according to the first embodiment, wherein the fusion protein is a mutated fusion protein prepared by amino acid substitution, deletion or insertion in the amino acid sequence of SEQ ID NO. 1, or a peptide analogue showing an activity similar to that of etanercept.

A fifth embodiment is the liquid formulation according to any one of the preceding embodiments, wherein the isotonic agent allows the liquid formulation to maintain an osmotic pressure of 280 to 350 mOsm.

A sixth embodiment is the liquid formulation according to any one of the preceding embodiments, wherein the isotonic agent contains sodium chloride (NaCl) and sucrose.

A seventh embodiment is the liquid formulation according to the sixth embodiment, wherein sodium chloride is present at a concentration of 1 to 1000 mM and sucrose is present in an amount of 0.01 to 3% by weight of the total composition.

An eight embodiment is the liquid formulation according to seventh embodiment, wherein sodium chloride is present at a concentration of 105 mM to 150 mM, and sucrose is present in an amount of 0.01 to 1.5% by weight of the total composition.

A ninth embodiment is the liquid formulation according to any one of the preceding embodiment, wherein the concentration of the fusion protein in the liquid formulation is in the range from 20 to 55 mg/mL.

A tenth embodiment is the liquid formulation according to any one of the preceding embodiments, wherein the buffer solution is a citrate-phosphate or phosphate buffer solution.

An eleventh embodiment is the liquid formulation according to the tenth embodiment, wherein the concentration of the buffer solution is in the range from 10 to 35 mM.

A twelfth embodiment is the liquid formulation according to any one of the preceding embodiments, wherein pH of the liquid formulation is in the range from 6.0 to 6.6.

A thirteenth embodiment is the liquid formulation according to any one of the preceding embodiments, wherein the formulation comprises proline at a concentration of less than 10 mM or histidine at a concentration of less than 5 mM.

A fourteenth embodiment is the liquid formulation according to the thirteenth embodiment, wherein the formulation comprises proline at a concentration of less than 9 mM or histidine at a concentration of less than 0.1 mM.

A fifteenth embodiment is the liquid formulation according to any one of first to fourteenth embodiments, wherein the formulation comprises a mixture of proline and histidine.

A sixteenth embodiment is the liquid formulation according to the fifteenth embodiment, wherein proline is present at a concentration from 1 mM to 9 mM and histidine is present at a concentration of less than 0.1 mM.

A seventeenth embodiment is the liquid formulation according to the sixteenth embodiment, wherein proline is present at a concentration of 1 mM to 9 mM and histidine is present at a concentration of 0.01 to 0.09 mM.

An eighteenth embodiment is the liquid formulation according to seventeenth embodiment, wherein proline is present at a concentration of 6 mM and histidine is present at a concentration of 0.09 mM.

A nineteenth embodiment is the liquid formulation according to any one of the first to thirteenth embodiments, further comprising glutamic acid at a concentration of 1 mM to 20 mM.

A twentieth embodiment is the liquid formulation according to nineteenth embodiment, wherein glutamic acid is present at a concentration of 10 to 15 mM.

A twenty first embodiment is a liquid formulation comprising TNFR-Fc fusion protein in a pharmaceutically effective amount, a citrate-phosphate buffer solution, sodium chloride, sucrose, and a mixture of amino acids comprising proline and histidine, wherein the TNFR-Fc fusion protein is a p75 sTNFR-Fc fusion protein.

A twenty second embodiment is the liquid formulation according to the twenty first embodiment, wherein the liquid formulation comprises 30 to 55 mg/mL of the TNFR-Fc fusion protein, and 10 to 35 mM citrate-phosphate buffer solution, 105 to 120 mM NaCl, 0.5 to 1.5% sucrose, 1 to 9 mM proline and 0.01 to 0.1 mM histidine and has a pH of 6.3.

A twenty third embodiment is the liquid formulation according to the twenty second embodiment, wherein the liquid formulation comprises 50 mg/mL of the TNFR-Fc fusion protein, 25 mM citrate-phosphate buffer, 115 mM NaCl, 1% of sucrose, 6 mM proline, and 0.09 mM histidine and has a pH of 6.3.

A twenty fourth embodiment is the liquid formulation according to the twenty first embodiment, wherein the liquid formulation comprises 30 to 55 mg/mL of TNFR-Fc fusion protein, and 10 to 35 mM citrate-phosphate buffer solution, 120 to 150 mM NaCl, 0.01 to 0.5% sucrose, 1 to 9 mM proline and 0.01 to 0.1 mM histidine and has a pH of 6.3.

A twenty fifth embodiment is the liquid formulation according to the twenty fourth embodiment, wherein the liquid formulation comprises 50 mg/mL of the TNFR-Fc fusion protein, 25 mM citrate-phosphate buffer, 130 mM NaCl, 0.1% of sucrose, 6 mM proline, and 0.09 mM histidine as the stabilizer and has a pH of 6.3.

A twenty sixth embodiment is the liquid formulation according to the twenty first embodiment, further comprising glutamic acid, wherein the liquid formulation comprises 30 to 55 mg/mL of the TNFR-Fc fusion protein, 10 to 35 mM citrate-phosphate buffer, 100-150 mM NaCl, 0.1 to 1.5% of sucrose, 5 to 15 mM glutamate, 1 to 10 mM proline, and 1 to 10 mM histidine and has a pH of 6.3.

A twenty seventh embodiment is the liquid formulation according to the twenty sixth embodiment, wherein the liquid formulation comprises 50 mg/mL of the TNFR-Fc fusion protein, 25 mM citrate-phosphate buffer, 100 mM NaCl, 1% of sucrose, 10 mM glutamate, 10 mM proline, and 5 mM histidine and has a pH of 6.3.

A twenty eight embodiment is a method for preparing a liquid formulation comprising a TNFR-Fc fusion protein of any one of claims 1 to 16, comprising:
  a) preparing the TNFR-Fc fusion protein; and
  b) mixing the TNFR-Fc fusion protein prepared in step a) with a stabilizer comprising one or more amino acids selected from the group consisting of proline and histidine, a buffer solution, and an isotonic agent containing sodium chloride (NaCl) and sucrose.

A twenty ninth embodiment is the method according to the twenty eight embodiment, wherein the mixing in step b) comprises i) preparing a solution comprising the stabilizer, the buffer solution, and the isotonic agent and ii) exchanging the solution in which the TNFR-Fc fusion protein is prepared in step a) with the solution in step i).

MODE FOR INVENTION

Hereinafter, the present invention will be described in more detail with reference to Examples. However, these Examples are for illustrative purposes only, and the invention is not intended to be limited by these Examples.

Example 1: Preparation of Etanercept Liquid Formulation

To stabilize a liquid formulation of the TNFR-Fc fusion protein, etanercept (recombinant p75 sTNFR:Fc fusion protein), an amino acid or mixture of amino acids was/were used as a stabilizer or an isotonic agent was controlled to examine the stabilizing effect. That is, liquid formulations were prepared by using proline or a mixture of proline and histidine as the stabilizer or by controlling the concentrations of NaCl and sucrose as the isotonic agent.

The liquid formulations of the present invention, in detail, Formulation 1 to Formulation 10 were prepared by adding one or more amino acids selected from the group consisting of, arginine, glutamic acid, proline and histidine to a 25 mM citrate-phosphate aqueous buffer solution and then adding sucrose and sodium chloride (NaCl) as an isotonic agent. Thereafter, pH of each formulation was adjusted to 6.3, and the formulations were subjected to dialysis so that the concentration of TNFR-fc fusion protein (etanercept) became 50 mg/mL, thereby preparing Formulation 1 to Formulation 10. Further, a control liquid formulation was prepared including 25 mM arginine, 100 mM sodium chloride and 1.0% sucrose as an isotonic agent in a 25 mM phosphate buffer solution also including 50 mg/mL etanercept, and then adjusting pH to 6.3. Thus, the control formulation was prepared, in which the etanercept concentration was 50 mg/mL.

The compositions of the prepared liquid formulations are as follows.

TABLE 1

Composition of liquid formulation

| Formulation | Etanercept conc. | Buffer solution | NaCl conc. | Sucrose conc. | pH | Amino acid |
|---|---|---|---|---|---|---|
| Formulation 1 | 50 mg/ml | 25 mM, Citrate-phosphate | 115 mM | 1.0% | 6.3 | — |
| Formulation 2 | 50 mg/ml | 25 mM, Citrate-phosphate | 115 mM | 1.0% | 6.3 | arginine 3 mM |
| Formulation 3 | 50 mg/ml | 25 mM, Citrate-phosphate | 115 mM | 1.0% | 6.3 | arginine 3 mM histidine 0.09 mM |
| Formulation 4 | 50 mg/ml | 25 mM, Citrate-phosphate | 115 mM | 1.0% | 6.3 | proline 3 mM |
| Formulation 5 | 50 mg/ml | 25 mM, Citrate-phosphate | 115 mM | 1.0% | 6.3 | proline 3 mM histidine 0.09 mM |
| Formulation 6 | 50 mg/ml | 25 mM, Citrate-phosphate | 140 mM | 0.1% | 6.3 | — |
| Formulation 7 | 50 mg/ml | 25 mM, Citrate-phosphate | 140 mM | 0.1% | 6.3 | proline 3 mM |
| Formulation 8 | 50 mg/ml | 25 mM, Citrate-phosphate | 140 mM | 0.1% | 6.3 | proline 3 mM histidine 0.09 mM |
| Formulation 9 | 50 mg/ml | 25 mM, Citrate-phosphate | 100 mM | 1.0% | 6.3 | glutamic acid 15 mM proline 5 mM histidine 5 mM |
| Formulation 10 | 50 mg/ml | 25 mM, Citrate-phosphate | 100 mM | 1.0% | 6.3 | glutamic acid 10 mM proline 10 mM histidine 5 mM |
| Control formulation | 50 mg/ml | 25 mM, phosphate | 100 mM | 1.0% | 6.3 | arginine 25 mM |

Example 2: Stability Test of Etanercept Liquid Formulations

To examine stability of the liquid formulations prepared in Example 1, each formulation was stored under the conditions of 25° C. and 40° C. for 1, 2, 4 and 8 weeks, and then the remaining amounts of etanercept were measured by size-exclusion high-performance liquid chromatography (SE-HPLC) and hydrophobic interaction high-performance liquid chromatography (HIC-HPLC).

The measurement results are shown in the following Tables 2 and 3.

TABLE 2

SE-HPLC for measurement of etanercept purity over time

| | | 25° C. | | | | | 40° C. | | | | |
|---|---|---|---|---|---|---|---|---|---|---|---|
| | Formulation | 0 wk | 1 wk | 2 wk | 4 wk | 8 wk | 0 wk | 1 wk | 2 wk | 4 wk | 8 wk |
| Reduction in etanercept purity (%) | 1 | 0.0 | −0.3 | −0.6 | −1.4 | −2.3 | 0.0 | −4.1 | −7.1 | −14.8 | −25.4 |
| | 2 | 0.0 | −0.2 | −0.5 | −1.3 | −2.1 | 0.0 | −4.0 | −6.8 | −13.6 | −24.2 |
| | 3 | 0.0 | −0.2 | −0.5 | −0.8 | −1.6 | 0.0 | −2.5 | −5.8 | −12.4 | −21.2 |
| | 4 | 0.0 | −0.3 | −0.6 | −1.4 | −2.4 | 0.0 | −4.1 | −7.1 | −14.4 | −24.8 |
| | 5 | 0.0 | −0.2 | −0.5 | −0.9 | −1.9 | 0.0 | −3.5 | −5.9 | −12.0 | −23.4 |
| | 6 | 0.0 | −0.2 | −0.6 | −1.4 | −2.3 | 0.0 | −4.1 | −6.9 | −13.5 | −22.4 |
| | 7 | 0.0 | −0.2 | −0.5 | −1.4 | −2.0 | 0.0 | −3.8 | −6.5 | −12.3 | −21.0 |
| | 8 | 0.0 | −0.1 | −0.4 | −0.8 | −1.6 | 0.0 | −3.3 | −5.7 | −11.4 | −20.3 |
| | 9 | 0.0 | −0.1 | −0.4 | −0.6 | −1.5 | 0.0 | −1.7 | −4.9 | −11.1 | −24.0 |
| | 10 | 0.0 | −0.1 | −0.4 | −0.7 | −1.3 | 0.0 | −1.9 | −5.2 | −11.2 | −24.6 |
| | Control | 0.0 | −0.2 | −0.5 | −1.1 | −2.2 | 0.0 | −3.8 | −6.6 | −13.9 | −25.7 |

TABLE 3

HIC-HPLC for measurement of etanercept purity over time

| | | 25° C. | | | | | 40° C. | | | | |
|---|---|---|---|---|---|---|---|---|---|---|---|
| | Formulation | 0 wk | 1 wk | 2 wk | 4 wk | 8 wk | 0 wk | 1 wk | 2 wk | 4 wk | 8 wk |
| Reduction in | 1 | 0.0 | −0.2 | −0.4 | −3.3 | −4.3 | 0.0 | −4.8 | −7.3 | −15.9 | −26.5 |
| | 2 | 0.0 | −0.2 | −0.4 | −3.2 | −4.2 | 0.0 | −4.7 | −7.1 | −14.7 | −25.6 |

TABLE 3-continued

HIC-HPLC for measurement of etanercept purity over time

|  | Formu-lation | 25° C. | | | | | 40° C. | | | | |
|---|---|---|---|---|---|---|---|---|---|---|---|
|  |  | 0 wk | 1 wk | 2 wk | 4 wk | 8 wk | 0 wk | 1 wk | 2 wk | 4 wk | 8 wk |
| etanercept purity (%) | 3 | 0.0 | −0.4 | −0.5 | −3.1 | −3.9 | 0.0 | −4.6 | −6.8 | −14.6 | −23.8 |
|  | 4 | 0.0 | −0.2 | −0.4 | −3.2 | −4.3 | 0.0 | −4.8 | −7.3 | −15.4 | −25.8 |
|  | 5 | 0.0 | −0.3 | −0.5 | −3.2 | −4.0 | 0.0 | −4.6 | −6.8 | −13.6 | −25.7 |
|  | 6 | 0.0 | −0.2 | −0.5 | −3.4 | −4.4 | 0.0 | −4.7 | −7.1 | −14.6 | −23.4 |
|  | 7 | 0.0 | −0.1 | −0.3 | −3.1 | −4.3 | 0.0 | −4.7 | −6.8 | −13.6 | −22.5 |
|  | 8 | 0.0 | −0.2 | −0.5 | −3.1 | −4.1 | 0.0 | −4.7 | −6.6 | −13.4 | −22.5 |
|  | 9 | 0.0 | −0.2 | −0.4 | N/A | −3.7 | 0.0 | −4.5 | −8.4 | −14.6 | −28.6 |
|  | 10 | 0.0 | −0.1 | −0.4 | −3.1 | −3.4 | 0.0 | −4.6 | −7.3 | −15.2 | −29.6 |
|  | Control | 0.0 | −0.1 | −0.3 | −3.4 | −4.7 | 0.0 | −5.0 | −8.0 | −16.4 | −29.5 |

※ N/A: Not Available

As confirmed in Tables 2 and 3 which show the analysis results of SE-HPLC and HIC-HPLC at 25° C. and 40° C., formulations using a mixture of the amino acids of proline and histidine (Formulation 5, Formulation 8) showed effects of improving stability of the etanercept solution, compared to the control formulation which was prepared by using arginine alone as a stabilizer in the composition of the conventional etanercept formulation.

These results demonstrated that the etanercept liquid formulation comprising a mixture of the amino acids of proline and histidine as a stabilizer prevents denaturation of etanercept to maintain its activity for a long period of time, and a mixture of the amino acids of proline and histidine is effective as a stabilizer in the stability improvement of the etanercept solution.

Further, etanercept stabilities were examined between the formulations of the present invention which were prepared by varying the composition of sucrose and sodium chloride of the isotonic agent in the composition of the conventional etanercept formulation. The formulation having a higher concentration of sodium chloride and a lower concentration of sucrose showed effects of improving stability of the etanercept solution, compared to the control formulation.

Furthermore, the liquid formulations using a mixture of the amino acids of proline and histidine as a stabilizer (Formulation 5 and Formulation 8) showed effects of improving stability of the etanercept solution, compared to the liquid formulations (Formulation 1 and Formulation 6) without the amino acid stabilizer.

Consequently, these experimental results showed that stability of the etanercept solution can be improved by 1) increasing the NaCl concentration and reducing the sucrose concentration in the isotonic agent and 2) using a mixture of the amino acids of proline and histidine as a stabilizer in the etanercept liquid formulation. That is, through the conditions of 1) or 2), formation of etanercept by-products can be effectively prevented and its stability can be improved so as to stably maintain pharmaceutical efficacy of etanercept for a long period of time, compared to the conventional etanercept liquid formulation.

Example 3: Stability Test of Etanercept Liquid Formulations Having a Composition of a Mixture of Amino Acids During Long-Term Storage Etanercept liquid formulations comprising one or more amino acids selected from proline and histidine and mixtures thereof, of which stability improvements were confirmed by the experiments of Examples 1 and 2, were subjected to a stability test under long-term storage conditions for 6 months.

In detail, a mixture of amino acids containing 0.09 mM histidine and 3 mM proline or a mixture of 0.09 mM histidine and 3 mM arginine were added to a 25 mM citrate-phosphate buffer solution, and 1.0% or 0.1% sucrose and 115 mM or 130 mM sodium chloride were also added thereto as an isotonic agent. Thereafter, pH of each formulation was adjusted to 6.3, and the formulations were subjected to dialysis so that the concentration of TNFR-fc fusion protein (etanercept) became 50 mg/mL, thereby preparing Formulation 1 to Formulation 3. Further, a control liquid formulation was prepared including 25 mM arginine, 100 mM sodium chloride and 1.0% sucrose as an isotonic agent in a 25 mM phosphate buffer solution also containing etanercept, and then adjusting pH to 6.3. Thus, the control formulation was prepared, in which the etanercept concentration was 50 mg/mL.

The compositions of the prepared liquid formulations are the same as in the following Table 4.

TABLE 4

Composition of liquid formulation for long-term storage

| | Composition of formulation | | | | | |
|---|---|---|---|---|---|---|
| Formulation | Etanercept conc. | Buffer solution | NaCl conc. | Sucrose conc. | pH | Amino acid |
| Formulation 1 | 50 mg/ml | 25 mM, Citrate-phosphate | 115 mM | 1.0% | 6.3 | arginine 3 mM histidine 0.09 mM |
| Formulation 2 | 50 mg/ml | 25 mM, Citrate-phosphate | 115 mM | 1.0% | 6.3 | proline 3 mM histidine 0.09 mM |

TABLE 4-continued

Composition of liquid formulation for long-term storage

| Formulation | Etanercept conc. | Buffer solution | NaCl conc. | Sucrose conc. | pH | Amino acid |
|---|---|---|---|---|---|---|
| Formulation 3 | 50 mg/ml | 25 mM, Citrate-phosphate | 130 mM | 0.1% | 6.3 | proline 3 mM histidine 0.09 mM |
| Control formulation | 50 mg/ml | 25 mM, phosphate | 100 mM | 1.0% | 6.3 | arginine 25 mM |

To examine stabilities of the liquid formulations prepared as in Table 4, each of the formulations was stored under the conditions of 4° C., 25° C. and 40° C. for 1, 3 and 6 months (under the condition of 40° C. for 3 months), and then the remaining amounts of etanercept were measured by size-exclusion high-performance liquid chromatography (SE-HPLC) and hydrophobic interaction high-performance liquid chromatography (HIC-HPLC).

The measurement results are shown in the following Tables 5 and 6.

TABLE 5

SE-HPLC for measurement of etanercept purity over time in mixed amino acid liquid formulations with improved stability

| | Formu-lation | 4° C. | | | | 25° C. | | | | 40° C. | | |
|---|---|---|---|---|---|---|---|---|---|---|---|---|
| | | 0 M | 1 M | 3 M | 6 M | 0 M | 1 M | 3 M | 6 M | 0 M | 1 M | 3 M |
| Reduction in etanercept purity (%) | 1 | 0.0 | −0.3 | −0.6 | −1.4 | 0.0 | −2.1 | −5.2 | −8.9 | 0.0 | −10.4 | −25.2 |
| | 2 | 0.0 | −0.4 | −0.7 | −1.4 | 0.0 | −2.2 | −6.1 | −9.5 | 0.0 | −10.0 | −25.3 |
| | 3 | 0.0 | −0.3 | −0.6 | −1.4 | 0.0 | −2.2 | −5.4 | −9.3 | 0.0 | −10.2 | −27.9 |
| | Control | 0.0 | −0.4 | −0.7 | −1.4 | 0.0 | −2.2 | −5.6 | −9.9 | 0.0 | −12.5 | −27.4 |

TABLE 6

HIC-HPLC for measurement of etanercept purity over time in mixed amino acid liquid formulations with improved stability

| | Formu-lation | 4° C. | | | | 25° C. | | | | 40° C. | | |
|---|---|---|---|---|---|---|---|---|---|---|---|---|
| | | 0 M | 1 M | 3 M | 6 M | 0 M | 1 M | 3 M | 6 M | 0 M | 1 M | 3 M |
| Reduction in etanercept purity (%) | 1 | 0.0 | −0.2 | −0.2 | −0.7 | 0.0 | −1.7 | −3.8 | −8.8 | 0.0 | −9.5 | −26.5 |
| | 2 | 0.0 | −0.2 | −0.3 | −0.8 | 0.0 | −1.8 | −4.3 | −8.7 | 0.0 | −8.9 | −25.9 |
| | 3 | 0.0 | −0.3 | −0.3 | −0.7 | 0.0 | −1.7 | −4.3 | −9.1 | 0.0 | −9.2 | −29.9 |
| | Control | 0.0 | −0.2 | −0.2 | −0.8 | 0.0 | −1.7 | −4.5 | −9.9 | 0.0 | −11.8 | −28.6 |

Also, in order to determine thermal stability of etanercept in the formulations as described in Table 4, and determine the temperature at which the etanercept protein unfolds, the thermograms of etanercept were measured by differential scanning calorimetry (DSC). FIG. 2 shows the DSC thermogram of each formulations at 6 month time point at 4° C. (FIG. 2A) and at 25° C. (FIG. 2B).

Three thermal unfolding states with transition temperatures of Tm1, Tm2, and Tm3 were evident, which indicated the presence of two domains originating from the Fc component of etanercept containing the domain of CH2 (Tm2), CH3 (Tm3), and extra-cellular ligand binding protein, tumor necrosis factor receptor (TNFR; Tm1) (N. A. Kim et al., Int. J. Pharm., 460(1-2), 108-118, 2014).

As shown in FIG. 2, formulation 1 using a mixture of arginine and histidine at 25° C. (FIG. 2B) showed that the valley between Tm1 and Tm2 peaks disappeared between storage at 4° C. (FIG. 2A) and at 25° C. (FIG. 2B) compared to the control formulation and the other formulations using a mixture proline and histidine. This result showed a decreased stability of CH2 domain in Fc component and extra-cellular ligand binding domain (TNFR) of etanercept in formulation 1.

Further, as confirmed in Tables 5 and 6 which show the analysis results of SE-HPLC and HIC-HPLC at 25° C. and 40° C., formulations using a mixture of the amino acids of proline and histidine (Formulations 2 and 3) showed effects of improving stability of the etanercept solution, compared to the control formulation which was prepared by using arginine alone as a stabilizer in the composition of the conventional etanercept formulation.

These results demonstrated that the etanercept liquid formulation comprising a mixture of the amino acids of proline and histidine as a stabilizer prevents denaturation of etanercept to maintain its activity for a long period of time.

Example 4: Stability Test of Etanercept Liquid Formulations According to Composition Ratio of Mixed Amino Acids To examine stabilities of the etanercept liquid formulations comprising the mixture of proline and histidine according to the composition ratio of the mixture of amino acids, in which these formulations were confirmed to have improved stability compared to the conventional etanercept formulation (single formulation containing arginine alone) in Examples 1 to 3, the stabilizing effect according to the composition ratio of the mixture of amino acids were examined. That is, liquid formulations were prepared by mixing proline and histidine as a stabilizer at various concentrations, and by controlling the concentrations of sucrose and sodium chloride as an isotonic agent.

In detail, to a 25 mM citrate-phosphate buffer solution, a mixture of the amino acids of 0.09 mM histidine and 3 mM to 9 mM proline as a stabilizer were added and 0.5% or 0.1% sucrose and 115 mM or 130 mM sodium chloride were added as an isotonic agent. Thereafter, pH of each formulation was adjusted to 6.3, and the formulations were subjected to dialysis so that the concentration of TNFR-fc fusion protein (etanercept) became 50 mg/mL, thereby preparing Formulation 1 to Formulation 5. Further, a control liquid formulation was prepared including 25 mM arginine, 100 mM sodium chloride and 1.0% sucrose as an isotonic agent in a 25 mM phosphate buffer solution containing 50 mg/mL etanercept, and then adjusting pH to 6.3. Thus, the control formulation was prepared, in which the etanercept concentration was 50 mg/mL.

The compositions of the prepared liquid formulations are the same as in the following Table 7.

TABLE 7

Composition of liquid formulation according to amino acid composition ratio of proline and histidine

| Formulation | Etanercept conc. | Buffer solution | NaCl conc. | Sucrose conc. | pH | Amino acid |
|---|---|---|---|---|---|---|
| Formulation 1 | 50 mg/ml | 25 mM, Citrate-phosphate | 115 nM | 0.5% | 6.3 | |
| Formulation 2 | 50 mg/ml | 25 mM, Citrate-phosphate | 115 nM | 0.5% | 6.3 | proline 3 mM histidine 0.09 mM |
| Formulation 3 | 50 mg/ml | 25 mM, Citrate-phosphate | 115 nM | 0.5% | 6.3 | proline 6 mM histidine 0.09 mM |
| Formulation 4 | 50 mg/ml | 25 mM, Citrate-phosphate | 115 nM | 0.5% | 6.3 | proline 9 mM histidine 0.09 mM |
| Formulation 5 | 50 mg/ml | 25 mM, Citrate-phosphate | 130 nM | 0.1% | 6.3 | |
| Formulation 6 | 50 mg/ml | 25 mM, Citrate-phosphate | 130 nM | 0.1% | 6.3 | proline 3 mM histidine 0.09 mM |
| Formulation 7 | 50 mg/ml | 25 mM, Citrate-phosphate | 130 nM | 0.1% | 6.3 | proline 6 mM histidine 0.09 mM |
| Control formulation | 50 mg/ml | 25 mM, phosphate | 100 nM | 1.0% | 6.3 | arginine 25 mM |

To examine stabilities of the liquid formulations prepared as in Table 7, each of the formulations was stored under the conditions of 25° C. and 40° C. for 2, 4 and 8 weeks and then the remaining amounts of etanercept were measured by size-exclusion high-performance liquid chromatography (SE-HPLC) and hydrophobic interaction high-performance liquid chromatography (HIC-HPLC).

The measurement results are shown in the following Tables 8 and 9.

TABLE 8

SE-HPLC for measurement of etanercept purity over time in liquid formulation according to change in amino acid composition ratio of proline and histidine

| | | 25° C. | | | | 40° C. | | | |
|---|---|---|---|---|---|---|---|---|---|
| | Formulation | 0 wk | 2 wk | 4 wk | 8 wk | 0 wk | 2 wk | 4 wk | 8 wk |
| Reduction in etanercept purity (%) | 1 | 0.0 | −1.3 | −2.3 | −3.9 | 0.0 | −6.1 | −10.9 | −19.0 |
| | 2 | 0.0 | −1.1 | −2.0 | −3.4 | 0.0 | −5.3 | −10.0 | −18.0 |
| | 3 | 0.0 | −1.2 | −2.0 | −3.4 | 0.0 | −5.2 | −10.0 | −18.0 |
| | 4 | 0.0 | −1.3 | −2.2 | −3.7 | 0.0 | −5.5 | −9.9 | −18.1 |
| | 5 | 0.0 | −1.3 | −2.4 | −4.0 | 0.0 | −5.5 | −10.2 | −18.0 |
| | 6 | 0.0 | −1.2 | −2.1 | −3.6 | 0.0 | −5.5 | −10.2 | −18.0 |
| | 7 | 0.0 | −1.2 | −2.1 | −3.6 | 0.0 | −5.2 | −9.7 | −17.7 |
| | Control | 0.0 | −1.3 | −2.4 | −4.0 | 0.0 | −6.3 | −11.4 | −19.8 |

TABLE 9

HIC-HPLC for measurement of etanercept purity over time in liquid formulation according to change in amino acid composition ratio of proline and histidine

| | | 25° C. | | | | 40° C. | | | |
|---|---|---|---|---|---|---|---|---|---|
| | Formulation | 0 wk | 2 wk | 4 wk | 8 wk | 0 wk | 2 wk | 4 wk | 8 wk |
| Reduction in etanercept purity (%) | 1 | 0.0 | −0.9 | −1.6 | −3.0 | 0.0 | −5.7 | −10.6 | −19.0 |
| | 2 | 0.0 | −0.9 | −1.5 | −3.1 | 0.0 | −5.3 | −10.2 | −19.0 |
| | 3 | 0.0 | −0.8 | −1.4 | −3.0 | 0.0 | −5.1 | −10.0 | −17.8 |
| | 4 | 0.0 | −1.0 | −1.6 | −2.8 | 0.0 | −5.1 | −9.5 | −18.2 |

TABLE 9-continued

HIC-HPLC for measurement of etanercept purity over time in liquid formulation according to change in amino acid composition ratio of proline and histidine

| Formu- | 25° C. | | | | 40° C. | | | |
| --- | --- | --- | --- | --- | --- | --- | --- | --- |
| lation | 0 wk | 2 wk | 4 wk | 8 wk | 0 wk | 2 wk | 4 wk | 8 wk |
| 5 | 0.0 | −0.9 | −1.6 | −2.9 | 0.0 | −5.6 | −10.4 | −18.7 |
| 6 | 0.0 | −0.8 | −1.5 | −3.0 | 0.0 | −5.3 | −10.1 | −18.4 |
| 7 | 0.0 | −0.8 | −1.5 | −3.1 | 0.0 | −5.4 | −9.6 | −18.0 |
| Control | 0.0 | −1.1 | −1.8 | −3.1 | 0.0 | −6.4 | −11.4 | −20.3 |

As confirmed in Tables 8 and 9 which show the analysis results of SE-HPLC and HIC-HPLC at 25° C. and 40° C., formulations using a mixture of the amino acids of proline and histidine showed effects of improving stability of the etanercept solution, compared to the control formulation which was prepared by using arginine alone as a stabilizer in the composition of the conventional etanercept formulation.

When the effect of improving stability according to the concentration ratio of the mixed amino acids used as a stabilizer was examined, the formulation (Formulation 3) prepared by mixing 6 mM proline and 0.09 mM histidine showed the most improved stability among the formulations comprising mixed amino acids of proline and histidine (Formulation 2 to Formulation 4) which were prepared by using 115 mM sodium chloride and 0.5% sucrose and varying the proline concentration from 3 mM to 9 mM.

These results demonstrated that the etanercept liquid formulation comprising mixed amino acids of 6 mM proline and 0.09 mM histidine as a stabilizer, as shown in the above composition ratio of proline and histidine, prevents denaturation of etanercept to maintain its activity for a long period of time.

Taken together, the present invention demonstrated that the etanercept liquid formulation comprising mixed amino acids of proline and histidine as a stabilizer prevents denaturation to maintain its activity for a long period of time, and the stability of the etanercept solution can be improved by using an isotonic agent consisting of a high concentration of sodium chloride and a low concentration of sucrose.

Based on the above description, it will be understood by those skilled in the art that the present invention may be implemented in a different specific form without changing the technical spirit or essential characteristics thereof. Therefore, it should be understood that the above embodiment is not limitative, but illustrative in all aspects. The scope of the invention is defined by the appended claims rather than by the description preceding them, and therefore all changes and modifications that fall within metes and bounds of the claims, or equivalents of such metes and bounds are therefore intended to be embraced by the claims.

The invention claimed is:

1. A liquid formulation comprising a TNFR-Fc fusion protein, one or more amino acids, a buffer solution, and an isotonic agent, wherein the fusion protein has the amino acid sequence of SEQ ID NO. 1, the concentration of the fusion protein is in the range from 20 to 55 mg/mL, and the formulation comprises a mixture of proline at a concentration of 1 mM to 9 mM and histidine at a concentration of 0.01 to 0.09 mM.

2. The liquid formulation according to claim 1, wherein the fusion protein is etanercept.

3. The liquid formulation of claim 1, wherein the isotonic agent allows the liquid formulation to maintain an osmotic pressure of 280 to 350 mOsm.

4. The liquid formulation of claim 1, wherein the isotonic agent contains sodium chloride (NaCl) and sucrose.

5. The liquid formulation of claim 4, wherein sodium chloride is present at a concentration of 1 to 1000 mM and sucrose is present in an amount of 0.01 to 3% by weight of the formulation.

6. The liquid formulation of claim 5, wherein sodium chloride is present at a concentration of 105 mM to 150 mM, and sucrose is present in an amount of 0.01 to 1.5% by weight of the formulation.

7. The liquid formulation of claim 1, wherein the buffer solution is a citrate-phosphate or phosphate buffer solution.

8. The liquid formulation of claim 7, wherein the concentration of the buffer solution is in the range from 10 to 35 mM.

9. The liquid formulation according to claim 8, wherein pH of the liquid formulation is in the range from 6.0 to 6.6.

10. The liquid formulation of claim 1, wherein the formulation comprises proline at a concentration of less than 10 mM or histidine at a concentration of less than 5 mM.

11. The liquid formulation of claim 10, wherein the formulation comprises proline at a concentration of less than 9 mM or histidine at a concentration of less than 0.1 mM.

12. The liquid formulation according to claim 1, wherein proline is present at a concentration of 6 mM and histidine is present at a concentration of 0.09 mM.

13. The liquid formulation of claim 1, further comprising glutamic acid at a concentration of 1 mM to 20 mM.

14. The liquid formulation of claim 13, wherein glutamic acid is present at a concentration of 10 to 15 mM.

15. A method for preparing a liquid formulation comprising a TNFR-Fc fusion protein of claim 1, comprising:
   a) preparing the TNFR-Fc fusion protein; and
   b) mixing the TNFR-Fc fusion protein prepared in step a) with a stabilizer comprising one or more amino acids selected from the group consisting of proline and histidine, a buffer solution, and an isotonic agent containing sodium chloride (NaCl) and sucrose.

16. The method according to claim 15, wherein the mixing in step b) comprises i) preparing a solution comprising the stabilizer, the buffer solution, and the isotonic agent and ii) exchanging the solution in which the TNFR-Fc fusion protein is prepared in step a) with the solution in step i).

17. A liquid formulation comprising TNFR-Fc fusion protein in a pharmaceutically effective amount, a citrate-phosphate buffer solution, sodium chloride, sucrose, and a mixture of amino acids comprising proline and histidine, wherein the TNFR-Fc fusion protein is a p75 sTNFR-Fc fusion protein.

18. The liquid formulation of claim 17, wherein the liquid formulation comprises 30 to 55 mg/mL of the TNFR-Fc fusion protein, and 10 to 35 mM citrate-phosphate buffer solution, 105 to 120 mM NaCl, 0.5 to 1.5% sucrose, 1 to 9 mM proline and 0.01 to 0.1 mM histidine and has a pH of 6.3.

19. The liquid formulation of claim 18, wherein the liquid formulation comprises 50 mg/mL of the TNFR-Fc fusion protein, 25 mM citrate-phosphate buffer, 115 mM NaCl, 1% of sucrose, 6 mM proline, and 0.09 mM histidine and has a pH of 6.3.

20. The liquid formulation according to claim 17, wherein the liquid formulation comprises 30 to 55 mg/mL of TNFR-Fc fusion protein, and 10 to 35 mM citrate-phosphate buffer solution, 120 to 150 mM NaCl, 0.01 to 0.5% sucrose, 1 to 9 mM proline and 0.01 to 0.1 mM histidine and has a pH of 6.3.

21. The liquid formulation according to claim 20, wherein the liquid formulation comprises 50 mg/mL of the TNFR-Fc fusion protein, 25 mM citrate-phosphate buffer, 130 mM NaCl, 0.1% of sucrose, 6 mM proline, and 0.09 mM histidine as the stabilizer and has a pH of 6.3.

22. The liquid formulation according to claim 17, further comprising glutamic acid, wherein the liquid formulation comprises 30 to 55 mg/mL of the TNFR-Fc fusion protein, 10 to 35 mM citrate-phosphate buffer, 100-150 mM NaCl, 0.1 to 1.5% of sucrose, 5 to 15 mM glutamate, 1 to 10 mM proline, and 1 to 10 mM histidine and has a pH of 6.3.

23. The liquid formulation according to claim 22, wherein the liquid formulation comprises 50 mg/mL of the TNFR-Fc fusion protein, 25 mM citrate-phosphate buffer, 100 mM NaCl, 1% of sucrose, 10 mM glutamate, 10 mM proline, and 5 mM histidine and has a pH of 6.3.

24. A liquid formulation comprising a TNFR-Fc fusion protein, one or more amino acids, a buffer solution, and an isotonic agent, wherein the fusion protein has the amino acid sequence of SEQ ID NO. 1 and the concentration of the protein is in the range from 20 to 55 mg/mL, and wherein the amino acids comprise proline at a concentration of 1 mM to 9 mM; histidine at a concentration of 0.01 to 0.09 mM; or a combination thereof.

* * * * *

SEQUENCE LISTING

```
<160> NUMBER OF SEQ ID NOS: 1

<210> SEQ ID NO 1
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Etanercept amino acid

<400> SEQUENCE: 1

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asp Thr Thr Ser Ser Thr Asp Ile Cys Arg Pro His
145                 150                 155                 160
```

```
Gln Ile Cys Asn Val Val Ala Ile Pro Gly Asp Ala Ser Met Asp Ala
            165                 170                 175
Val Cys Thr Ser Thr Ser Pro Thr Arg Ser Met Ala Pro Gly Ala Val
            180                 185                 190
His Leu Pro Gln Pro Val Ser Thr Arg Ser Gln His Thr Gln Pro Thr
            195                 200                 205
Pro Glu Pro Ser Thr Ala Pro Ser Thr Ser Phe Leu Leu Pro Met Gly
        210                 215                 220
Pro Ser Pro Pro Ala Glu Gly Ser Thr Gly Asp Glu Pro Lys Ser Cys
225                 230                 235                 240
Asp Lys Thr His Thr Cys Pro Pro Cys Pro Ala Pro Glu Leu Leu Gly
            245                 250                 255
Gly Pro Ser Val Phe Leu Phe Pro Pro Lys Pro Lys Asp Thr Leu Met
            260                 265                 270
Ile Ser Arg Thr Pro Glu Val Thr Cys Val Val Val Asp Val Ser His
            275                 280                 285
Glu Asp Pro Glu Val Lys Phe Asn Trp Tyr Val Asp Gly Val Glu Val
        290                 295                 300
His Asn Ala Lys Thr Lys Pro Arg Glu Glu Gln Tyr Asp Ser Thr Tyr
305                 310                 315                 320
Arg Val Val Ser Val Leu Thr Val Leu His Gln Asp Trp Leu Asn Gly
            325                 330                 335
Lys Glu Tyr Lys Cys Lys Val Ser Asn Lys Ala Leu Pro Ala Pro Ile
            340                 345                 350
Glu Lys Thr Ile Ser Lys Ala Lys Gly Gln Pro Arg Glu Pro Gln Val
            355                 360                 365
Tyr Thr Leu Pro Pro Ser Arg Glu Glu Met Thr Lys Asn Gln Val Ser
    370                 375                 380
Leu Thr Cys Leu Val Lys Gly Phe Tyr Pro Ser Asp Ile Ala Val Glu
385                 390                 395                 400
Trp Glu Ser Asn Gly Gln Pro Glu Asn Asn Tyr Lys Thr Thr Pro Pro
            405                 410                 415
Val Leu Asp Ser Asp Gly Ser Phe Phe Leu Tyr Ser Lys Leu Thr Val
            420                 425                 430
Asp Lys Ser Arg Trp Gln Gln Gly Asn Val Phe Ser Cys Ser Val Met
            435                 440                 445
His Glu Ala Leu His Asn His Tyr Thr Gln Lys Ser Leu Ser Leu Ser
    450                 455                 460
Pro Gly
465
```